United States Patent [19]

Lefrancier

[11] 4,107,158

[45] Aug. 15, 1978

[54] PROCESS FOR MAKING AN OCTAPEPTIDE USEFUL FOR THE TREATMENT OF DIABETES

[75] Inventor: Pierre Lefrancier, Bures-sur-Yvette, France

[73] Assignee: Choay S.A., Paris, France

[21] Appl. No.: 644,844

[22] Filed: Dec. 29, 1975

[30] Foreign Application Priority Data

Dec. 31, 1974 [FR] France .................. 74 43513

[51] Int. Cl.² .................. C07C 103/52; A61K 37/00
[52] U.S. Cl. .................. 260/112.5 R; 260/112.7; 424/177; 424/178
[58] Field of Search .................. 260/112.5 R

[56] References Cited

U.S. PATENT DOCUMENTS

| 3,928,306 | 12/1975 | Uchijama et al. | 260/112.5 R |
| 3,953,415 | 4/1976 | Kisfaludy et al. | 260/112.5 R |
| 3,978,035 | 8/1976 | Wunsch et al. | 260/112.5 R |

OTHER PUBLICATIONS

E. Schröder and K. Lubke, "The Peptides," vol. 1, Academic Press, New York, 1965, pp. 1-2.
J. M. Stewart and J. D. Young, "Solid Phase Peptide Synthesis," W. H. Freeman & Co., San Francisco, 1969, pp. 3-5.

*Primary Examiner*—Delbert R. Phillips
*Attorney, Agent, or Firm*—Weiser, Stapler & Spivak

[57] ABSTRACT

Process for the preparation of the compound consisting of the peptide chain: leucyl — seryl — arginyl — leucyl — phenylalanyl — aspartyl — asparaginyl — alanine (I), characterized in that the synthesis is carried out from constituent amino-acids of the peptide chain (I), or from peptide elements resulting from the condensation of two or several of these basic amino-acids, and by the condensation of these amino-acids or peptide elements, in a succession of steps so that the basic amino-acids occur in the final peptide chain in the order indicated in (I).

21 Claims, No Drawings

PROCESS FOR MAKING AN OCTAPEPTIDE USEFUL FOR THE TREATMENT OF DIABETES

The invention relates to a novel glycemia regulating agent of the peptide type. It also relates to processes for obtaining this agent and to pharmaceutical compositions which contain it.

The factors which influence glycemia are numerous and the mechanisms that they control are particularly complex and, for certain of them, moreover, unelucidated.

Insulin, of course, plays a preponderant role in the regulation of glycemia. It is also known that numerous cases of diabetes are due either to insufficient production of insulin by the organism, or to inhibition of its activity under the effect of natural agents whose production by the organism tends to become disturbed, notably to become excessive. Among these agents are certain degradation products of the growth hormone which is found in the plasma, such as, notably, the peptide chain known by the name of somantine.

It is an object of the invention to provide a new medicament whose main action is to counter the effect of natural inhibitors of insulin. It is also an object to provide a medicament which tends to regulate the hypoglycemic activity of insulin.

According to the invention, these objects are achieved with the product constituted by the α-peptide chain of the following L aminoacids: leucyl—seryl—arginyl—leucyl—phenylalanyl—aspartyl—asparaginyl-alanine (I).

The preparation of this chain is effected by synthesis, starting from the constituent amino-acids of the peptide chain of the invention, or from peptide elements resulting from the condensation of two or several of these basic amino-acids, and by condensation of these amino-acids or peptide elements, in a succession of steps such that the basic amino-acids occur in the final peptide chain in the order indicated in the formula (1).

According to a preferred method of preparation, the synthesis can be carried out in homogeneous phase, that is to say a solution in a solvent in which the derivatives of the amino-acids or of the peptide elements utilised are soluble.

According to another advantageous method of preparation, the synthesis is carried out in the solid phase and more particularly according to the technique, inter-alia, of Stewart and Young (Solid Phase Peptide Synthesis, San Francisco, W. H. Freeman, 1969).

The synthesis of well-defined peptide chains, not only in the nature and in the order of their constituents, but also in their stereospecificity, poses numerous problems. It is known, in fact, that condensation reactions between two amino-acids or two peptide fragments bring about racemisations. A traditional method for the synthesis of stereospecific chains consists of effecting the condensations in recurrent manner, starting at the end of the chain which carries the carboxylic group not involved in the peptide linkage. then, step by step, condensing all the constituent amino-acids.

This technique, which is applicable for the synthesis of the octapeptide of formula (I), has nevertheless some drawbacks and, in particular, the stage of the purification of the final product obtained. Condensation reactions are never perfect. The formation of interfering products which must be removed from the final product, is always encountered. The purification is all the more difficult as, for the same difference in molecular weight, the products to be separated are of higher molecular weight. The purification effected on the complete octapeptide chain in recurrent manner is hence, in the present case, that which raises most difficulties.

A usual method of checking the stereochemical structure of the synthesized peptide chains consists of carrying out stereospecific enzymatic hydrolysis, by means, notably, of an aminopeptidase such as, for example, leucine-aminopeptidase. Such hydrolysis leads to the systematic rupture of the L—L—peptide bond closest to the terminal amine group. Analysis of the hydrolysis products hence enables verification of the L—L— nature of the peptide bonds. Now it has been observed that leucine-aminopepticase does not hydrolyse the peptide chain(I), so that it was necessary to find a method of analysis enabling the stereospecificity of the octapeptide to be checked. Without this method, it was difficult, if not impossible, to determine those of the conditions, in particular those of the coupling sequences of the successive amino-acids or of the peptide fragments, which would finally enable the desired all —L—octapeptide to be reached.

It is the perfecting of this method of stereochemical analysis which has enabled the determination of the preferred methods of synthesis of the peptide chain (I), according to which the synthesis of two or three peptide fragments is first carried out, which are then condensed together to constitute the complete chain.

It has, in fact, been noted that it was possible, by enzymatic hydrolysis, to break the peptide chains at the level of certain well-determined peptide linkages and only when the chain formed belongs to the L series. When condensations of fragments at the level of these hydrolysable bonds are carried out, it is possible to be sure that the condensation selected does not lead to racemisation of the products, in other words, so that, by this reaction it is indeed the peptide of the desired L series which is obtained. For this, a specimen of the free-peptide derived from the condensation is subjected to enzymatic hydrolysis and the resulting products are analysed, for example by thin longer chromatography. When the reaction is indeed stereospecific, that is to say the product obtained is of the L series, it is hydrolysed and only the initial fragments are found again. If, on the contrary, the condensation leads partly at least to racemisation, non-hydrolysed peptide chain corresponding to the D isomer will be found in the hydrolysis products.

Advantageously, it will be possible to effect a condensation of fragments at the level of the peptide linkage :

phenylalanyl — aspartyl.

It was possible to show, in fact, by means of hydrolysis in the presence of chymotrypsin, that the condensation of fragments at this level occurred practically without racemisation.

Another advantageous method consists of carrying out the condensation of the fragments at the level of the linkage :

arginyl — leucyl.

In the same way as previously, the absence of racemisation at this level was checked by hydrolysis carried out, this time, in the presence of trypsin.

However, the most preferred embodiment of the synthesis of the peptide chain (I) consists of the separate preparation of the two fragments leucyl — seryl — arginyl — leucyl — phenyl —alanine, and aspartyl — asparaginyl — alanine, then of condensing these two fragments. So, other preferred embodiments consist of condensing the groups of the following fragments :

leucyl — seryl — arginyl and leucyl — phenylalanyl — aspartyl — asparaginyl —alanine or again :

leucyl — seryl — arginyl and leucyl — phenylalanine then aspartyl — asparaginyl — alanine.

The use of small-size fragments also makes purification easier, notably after the final condensation step. The removal of the initial fragments of the condensation product is, in fact, facilitated by the difference in molecular weight and in charge, existing between the latter.

The functions which must be protected, during the different processes of condensation of the amino-acids or peptide elements derived from prior condensations, are protected firstly by means of blocking groups which are removed once the condensation is completed. Such protective groups are, for example: benzyloxycarbonyle, t.butyloxycarbonyle, benzylester, etc. which groups can then be eliminated.

The choice of protective groups is a function of several factors such as simplicity of use, their cost or their efficiency ... Of course, they must, in addition, be removable without risk of degradation of the product prepared. Advantageously, hydrogenolysable groups are used for "long term" protection, that is to say, for blocking maintained for several successive reactions of those chemical functions borne by the amino-acids used, which are not brought into play in the synthesis reaction of the octapeptide. This is notably the case for the terminal acid function. Hydrogenolysable groups are, for example, benzyloxycarbonyl, benzyl ester groups, or nitro-groups. For short term protection, notably those of the amine functions which are only arranged for the duration of one condensation, acidolysable groups are advantageously used, such as the ter .butyloxycarbonyl group. Saponifiable groups are excluded from this choice by reason of the presence of aspartic acid in the octapeptide.

The long and short term groups must belong to different types so that the removal of the one does not simultaneously involve the removal of the others. However, it is possible on the other hand, in particular for the last condensation operation, to take groups of the same type to effect unblocking in a single operation.

According to preferred methods of synthesis of the compound according to the invention, procedure is either by direct condensation of the respectively amine and carboxylic groups of the amino-acides or peptide elements which must be coupled, in the presence of agents facilitating this direct condensation, for example, of dicyclohexyl-carbodiimide, or by resorting to prior activation of the carboxyl groups which must take part in the condensation. For example, the carboxyl groups can be esterified with an alcohol capable of supplying an "activated" ester function of this amino-acide, or it can be "activated" according to mixed-anhydride method.

It is the activated ester method which is preferred in the course of the synthesis for the condensation of asparagine. The use of dicyclohexyl carbodiimide could lead to an undesirable dehydration of the carboxamide function. As an example, the paranitrophenyl ester of asparagine is used.

In addition, on the condensation of fragments together, it is advantageous to introduce a product such as hydroxy-benzotriazole which enables racemisation, at least for the major part, to be avoided.

In the course of the synthesis and after each condensation, it is advantageous to isolate and to purify the condensation product formed. It is possible to carry out these operations, for example, by chromatography and by recrystallisation in suitable solvents.

By proceding with the synthesis according to the previously described method, a product is obtained, constituted almost entirely by the desired octapeptide ; however, if desired its purity can be improved further, advantageously in accordance with method of purification disclosed hereafter. The presence has been observed, by then longer chromatography, of a slight stain corresponding to the impurities and which is difficult to distinguish from that corresponding to octapeptide. To remove this impurity, chromatography on an ion exchange column filled with carboxy-methylcellulose is advantageously carried out. The amount of carboxy-methylcellulose that it contains must be sufficient to fix the whole of the specimen of product introduced (in aqueous solution).

The product is introduced into the column in solution in water. An elution with an amount of water corresponding to the half dead volume of the column permit a differential elution of the impurity and of the octapeptide, the impurities having a tendency under these conditions, to pass through before the octapeptide. Then the speed of elution is accelerated by using successively two more concentrated acid solutions. Advantageously, the concentration of the two acid solutions is respectively of the order of 0.05 M and 1 M.

The substance (1) is used in pharmaceutical compositions, if necessary in association with excipients and physiologically acceptable adjuvants and, if necessary also with other active agents.

The medicament thus constituted is useful in the treatment of certain forms of diabetes, for the purpose notably of regulating the interactions of secreted insulin with other agents, for example, of fractions of growth hormone having an antagonist effect with respect to insulin.

In a preferred particular embodiment of the invention, the latter relates also to a medicament associating, in the same form, insulin and the product according to the invention.

Other features of the invention will emerge also in the following description, in the light of a preferred embodiment for the preparation of the compound of formula (I) and of pharmacological tests which have permitted the establishment of the remarkable properties of this compound.

The process indicated below by way of example brings into play successive condensations of aminoacids or of peptide elements, either by the direct route, or by prior activation of functions coming into play in these condensations. Whatever the method of operation selected, the condensation products obtained (after filtration in the case of condensations carried out in the presence of dicyclohexyl-carbodiimide, for the purpose of removing the precipitated dicyclohexylurea is purified in the following manner.

The solvent is driven off under vacuum at 35° C. The oily or crystalline residue if taken up in ethyl acetate and washed successively with a 10% citric acid solution in distilled water, a solution of M NaH·CO$_3$, then with distilled water until neutral pH. The organic solution is dried over MgSO$_4$ for 20 minutes, then filtered or indeed filtered directly on hydrophobic paper (Schleicher and Schull). After concentration, the product can be crystallised.

The protecting groups, such as for example t.-butyloxycarbonyl, are removed in all cases by acid hydrolysis. In the same way, the hydrolysis has always been effected by means of a normal hydrochloric acid solution in acetic acid (20 minutes at ordinary temperature), the solution is concentrated to dryness, taken up several times in acetone and reconcentrated each time. The product obtained is dried under vacuum in a dessicator, in the presence of KOH; then it is generally crystallised in methanol-ether.

In the following description, the abbreviations used have the following significance:

| Z    | = benzyloxycarbonyl    | Leu = leucine        |
|------|------------------------|----------------------|
| BOC  | = t.-butyloxycarbonyl  | Ser = serine         |
| OBzl | = benzyl ester         | Arg = arginine       |
| OMe  | = methyl ester         | Ala = alanine        |
| DMF  | = NN'-dimethylformamide|                      |
| Phe  | = phenylalanine        |                      |
| Asn  | = asparagine           |                      |
| Asp  | = aspartic acid        |                      |

The preparation of the compound according to the invention has been carried out in the example concerned, by resorting to the preparation sequences described below.

1. Preparation of BOC—ASn—Ala—OBzl (I)

1.5 g (4.24 mmoles) of p-nitrophenyl ester of BOC—Asparagine are added to a solution cooled to 0° of 1.7 g (4.84 mmoles) of p-toluene sulfonate of the benzyl ester of alanine and of 0.53 ml (4.84 mmoles) of N-methylmorpholine, in 15 ml of dimethylformamide. After 24 hours at ambient temperature, the product is purified as described above. In suspension in ether, 1.33 g (79%O of the product is obtained after filtration, having a melting point and a rotatory power (in dimethyl formamide) respectively of m.p. 138°–141°; $\alpha_D^{25}$ = 17.5°(c = 1.02 DMF).

2. Preparation of HCl, Asn—Ala—OBzl (II)

1.33 g (3.38 mmoles) of (I) are treated with 10 ml of an N HCl solution in acetic acid, then as described above an 863 mg (79%) of product is obtained, whose melting point is m.p. 125°–136°.

3. Preparation of BOC—Asp(OBzl)—Asn—Ala—OBzl (III)

585 mg (1.8 mmole) of β-benzyl ester of BOC-aspartic acid are added to the solution, cooled to 0°, of 636 mg (1.9 mmole) of (II) and of 0.2 ml (1.9 mmole) of N-methylmorpholine in 10 ml of dimethyl formamide. After 24 hours at ambient temperature, the product is purified as described above. By crystallisation in ethyl acetate and petroleum ether, 680 mg (63%) of product are obtained, having a melting point and a rotatory power in dimethyl formamide of respectively : m.p. 128°–130°; $\alpha_D^{25}$ = 14.55° (c = 1.02 DMF).

Preparation of HCl, Asp (OBzl)—Asn—Ala—OBzl (IV)

572 mg (0.96 mmole) or (III) are treated with 5 ml of an N HCl solution of acetic acid then as described above, and 443 mg (87%) of product is obtained which decomposes at 195° and has a rotatory power in methanol of $\alpha_D^{25}$ = −15.7° (c = 1 Methanol).

Preparation of BOC—Leu—Phe—OMe (V)

4.26 g (20 mmoles) of BOC-Leucine then 4.33 g (21 moles) of dicyclohexylcarbodiimide are added to the solution cooled to 0° at 4.75 g (22 mmoles) of the methyl ester of phenylalanine and 2.4 ml (22 mmoles) of the methyl ester of phenylalanine and of 2.4 ml (22 mmoles) of N-methyl-morpholine in 30 ml of tetrahydrofurane. After 20 hours at ambiant temperature, the product is purified as described above, then it is crystallised in ethyl acetate and petroleum ether. 4.954 g (64%) of product are thus obtained, whose constants, melting point and rotatory power are : m.p. 87°, 88°; $\alpha_D^{25}$ = −19.5° (c = 1 DMF).

Preparation of HCl, Leu—Phe—OMe (VI)

4.417 g (11.3 mmoles of V are treated with 25 ml of an N HCl solution in acetic acid, then as described above. 2.980 g (81%) of product are obtained whose constants are: m.p. 190°–199°. $\alpha_D^{25}$ = +11° (c = 2 methanol.

7. Preparation of BOC—ARg(NO$_2$)—Leu—Phe—Ome (VII)

2.72 g (8.5 mmoles) of BOC(NO$_2$) arginine, then 1178 g (8.6 mmoles) of dicyclohexylcarbodiimide are added to a solution cooled to 0° of 2.98 g (91. mmoles) of (VI) and of 1 ml (9 mmoles) of N-methylmorpholine in 15 ml of dimethylformamide. After 20 hours of ambiant temperature the product is purified as described above, then it is crystallised in ethyl acetate and petroleum ether. 4.24 g of product (85%) are obtained. m.p. 95°. $\alpha_D^{25}$ = −10.9°(c = 1 methanol).

8. Preparation of HCl, Arg (NO$_2$)—Leu—Phe—Ome (VIII)

4.24 g (7.1 mmoles) of (VII) are treated with 20 ml of an N HCl solution in acetic acid, then as described above. 3.40 g of product are obtained. m.p. 150°. By recrystallisation in the mixture methanol-ether, 2.40 g of product (64%) are obtained. m.p. 198°—200°.

9. Preparation of BOC—Ser (OBzl)—Arg(NO$_2$) —leu—Phe—OMe (IX)

1.32 g (4.4 mmoles) of BOC—Ser(OBzl), then 660 mg (4.4 mmoles) of hydroxybenzotriazole and 908 mg (4.4 mmoles) of dicyclohexylcarbodiimide, are added to a solution cooled to 0° of 2.40 g (4.5 mmoles) of (VIII) and of 0.5 ml (4.5 mmoles) of N-methylmorpholine in 15 ml of methyl formamide. After 20 hours at ambiant temperature the product is purified as described above. 3.3 g of an oil (92%) are obtained.

10. Preparation of HCl, Ser(OBzl)—Arg(NO₂)—Leu—Phe—OMe (X)

3.3g (4.3 mmoles) of (IX) are treated with 15 ml of an N HCl solution in acetic acid, then as described above. 2.6 g of product mp 195°–200°. are obtained. After recrystallization in a methanol-acetate-petroleum ether mixture, 2.40 g of product (81%) are obtained. m.p. 200° $a_D^{25} = 15°$ ($c = 1$ methanol).

11. Preparation of BOC—Leu—Ser(OBzl)—Arg(NO₂)—Leu—Phe—OMe (XI)

832 mg (3.6 mmoles) of BOC—Leu (4), then 550 mg (3.6 mmoles) of hydroxybenzotriazole and 743 mg (3.6 mmoles) of dicyclohexylcarbodiimide, are added to a solution cooled to 0° of 2.6 g (3.65 mmoles) of (X) and of 0.40 ml 3.7 mmoles) of N-methylmorpholine in 10 ml of dimethylformamide. After 20 hours at ambiant temperature, the dicylohexylurea is filtered and the filtrate concentrated to dryness. The residue is taken up in aqueous ethyl acetate in which medium the product precipitates. It is however purified as described above. 2.18 g of the product (68%) are obtained. m.p. 184°–188° C. $a_D^{25} = -30.1°$ (c = 1 methanol).

12. Preparation of BOC—Leu—Ser(OBzl)—Arg(NO₂)—Leu—Phe—OX (XII)

450 mg (0.5 mmole) of (XI) are dissolved with heating in 4 ml of methanol. In the cold, 1 ml of an N solution of KOH is added. After 3 hours at ambiant temperature, 20 ml of water are added, then it is acidified in the cold with citric acid. The precipitate obtained is filtered and dried: 400 mg (90%). m.p. 107°–115° C $a_D^{25} = 19.2°$(c = 1 methanol).

13. Preparation of BOC—Leu—Ser(OBzl)—Arg(NO₂)—Leu—Phe—Asp()Bzl)—Asn—Ala—OBzl (XIII)

400 mg (0.45 mmole) of (XII), then 77 mg (0.5 mmole) of hydroxybenzotriazole and 103 mg (0.5 mmole) of dicyclohexylcarbodiimide, are added to a solution cooled to 0° of 300 mg (0.55 mmole) of (IV) and 0.06 ml (0.55 mmole) of N-methylmorpholine in 5 ml of dimethylformamide. After 24 hours at ambiant temperature, the dicyclohexylurea precipitated is filtered and the filtrate concentrated almost to dryness. By the addition of water, a precipitate is obtained which is filtered and dried, then recrystallised in DMF, ether and petroleum ether. 500 mg of product (81%) are obtained. Analysis of amino-acids of a total acid hydrolysate of this product (carried out in a sealed tube under vacuum at 110° for 24 hours in the presence of 6 N HCl) leads to the following result: Leu 1.9, Ser 0.9, Arg 1, Phe 0.9, Asp 2.1, Ala 1.2. m.p. 183°–185°. $a_D^{25} = 21°$ (c = 1, DMF)

14. Preparation of HCl, Leu—Ser—Arg—Leu—Phe—Asp—Asn—Ala (XIV)

430 mg (0.315 mmole) of (XIII) are taken up in 10 ml of acetic acid. In the presence of 5% palladium on carbon, a current of hydrogen is passed into the solution for 10 hours, The suspension is then filtered on celite and the filtrate, concentrated, is treated with 2 ml of an N HCl solution in acetic acid, then as described above: by precipitation with acetone 300 mg of product (92%) are obtained. 50 mg of the product obtained are taken up in 5 ml of a 2% acetic acid solution, then deposited on a column (1 × 20 cm) of an anion exchange resin which is weakly basic and of the type known in commerce by the name Amberlite IR 45 (acetate form), previously equilibrated with the same solvent as that which is used for elution. The tubes in which the product is collected are concentrated (or lyophilised). The residue is taken up in 1 ml of distilled water then deposited on a column (0.5 × 30 cm) of carboxymethylcellulose. It is diluted iwth 32 ml of water per fraction of 2 ml, then with 20 ml of an 0.05 M acetic acid solution. Finally, by means of a 1 M acetic acid soluton, it is eluted recovering the samples derived from the latter elution; after lyophilisation, 40 mg of product is obtained. The purity of the product is checked by chromotography on silica gel plates with the solvent A. The rotatory power of the product obtained is : $a_D^{25} = -14°$ (in glacial acetic acid).

Amino-acid analysis after total acid hydrolysis is: Leu 2.06 : Ser 0.95 ; Phe 0.98 ; Arg 0.97 ; Asp 2.11 ; Ala 1.04. It gives a yield of peptide of 95.6% (calculated 47.77 nmoles, found 45.67 nmoles).

In addition, at the end of the synthesis, a check of the stereospecificity of the fragments coupling reaction is carried out on a sample of the product. This check is done in the following manner.

About 1μ mole of peptide is incubated at 37° C in 0.5 ml of ammonium acetate buffer (pH 8.1) and 50 μg of α-chymotrypsin is added. After 20 hours 0.5 ml of acetic acid are added and the reaction mixture is lyphilised. The residue is taken up in 0.3 ml of distilled water and chromatographed on a silica gel plate in the mixture of solvents n butanol-pyridine-acetic acid-water (30 - 20 - 6 - 24 vol/vol).

The melting points were determined in capillary tubes with the apparatus of Dr. Tottoli (Ets Buchi Falwil — Suisse) and have not been corrected. The measurements of physical constants and the elementary analyses were carried out on the products dried under vacuum (10⁻² mm Hg) generally for 20 hours at 78°. The elementary analyses were done with a Perkin-Elmer automatic C.H.N. micro-analysis apparatus. The rotatory powers were determined by means of the Perkin-Elmer model 241 electronic polarimeter. The chromatographies were effected on fine plates of silica gel (Merck) in a mixture of solvents (A) : n-butanol-pyridine-acetic acid-water (30-20-6-24 v/v), or (B) : n-butanol-acetic acid-water (4-1-5 upper phase).

Below are described some of the pharmacological tests showing the excellant properties of the peptide of the formula (1) are, in particular, its role as "facilitating" the regulating effect of insulin with regard to glycemia.

a. Enzymatic effect in vitro

The inhibiting effect of degradation products of the growth hormone, notably somantine, is manifested with respect to various enzymes.

In this test, the compound (I) was tested for its ability to raise the inhibition of a somantine extracted from a plasma with respect to the action of glyceraldehyde 3-phosphate dehydrogenase.

To this end, the activity of the enzyme in the presence successively of somantine alone, of the compound (1) alone, and finally in the presence of somantine and of the compound (I), were measured.

In this test, the glyceraldehyde 3-phosphate dehydrogenase was used at a concentration of 0.5 μml, the somantine at 25 μg/ml, and the compound (I) at 50 μg/ml.

The method used for the measurements is that of Pihl and Lang (J. Biol. Chem 237 : 1356 – 1362, 1962).

The percentage of inhibition of the enzyme found under these conditions is as follows:

| | | |
|---|---|---|
| with somantine | 65.3% | (b) |
| with the compound (I) | 1.0% | |
| with somantine + the compound (I) | 48.2% | (c) |
| inversion ratio $\frac{b-c}{b} \times 100 = 26.2\%$ | | |

These results establish the inhibiting effect of somantine. On the other hand, the compound (I) is practically without effect on the activity of the enzyme. However, the compound (I) enables, when it is administered together with somantine, the inhibiting effect of somantine to be partly suppressed.

b. Consumption of glucose in vitro

To follow this consumption, the isolated hemidiaphragm of the rat in vitro was used. The method employed is that described by Park et al. (Effect of insulin on free glucose content of rat diaphragm in vitro — Amer. J. Physiol. 182 : 12 – 16, 1955).

The hemidiaphragm derived from Wistar albino male rats each weighing 200 to 250 g was used. The rats were fed freely for 7 days and then starved for 24 hours.

The solutions studied contained 2 mg/ml of glucose, 500 μU/ml of insulin. The compound (I) was introduced at 250 μg/ml.

The consumption of glucose related to the weight of tissue in grams and per hour was under these conditions:

| Solution | Consumption of glucose in mg |
|---|---|
| glucose | 2.26 ± 0.14 |
| glucose ± insulin | 4.10 ± 0.15 |
| glucose + insulin + compound (I) | 5.34 ± 0.17 |

From the foregoing, it is concluded that the consumption of glucose in the presence of insulin is increased in the presence of the compound (I).

c. Effect of the compound (I) on the in vivo effect of insulin

The assays were carried out in the course of the tests carried out to determine the resistance to glucose injected by the intravenous route in the rabbit.

These tests were done on adult rabbits, which had been subjected to prior fasting for 24 hours. Blood was drawn off and the glucose level in the blood samples was determined. The measurement was carried out by the ferricyanide method as adapted for the "Technicon Autoanalyser" (J. Biol. Chem. 120 : 51 – 55, 1937). In this way the glucose level on fasting, then its variation after the intravenous injection of glucose, at the dose of 1 gram per kilo, was determined. These measurements were then renewed in rabbits which had received, 5 minutes after the glucose, an intravenous injection of the compound (1) (5μg/kg).

These tests have shown that the decrease in the glucose level is greater for rabbits which have received compound (I). Again, for the latter, the glucose level even reached values less than those which were measured in the fasting rabbits.

Similar tests, carried out at intervals of several days, have also enabled it to be shown that an effect on the carbohydrate metabolism persists several days after the injection of compound (I).

d. Influence of octapeptide (I) on glycemia has been determined in mice under conditions similar to those described for rabbits. The experiment included two series of tests aimed at studying the immediate effects and the prolonged effects.

In the first series of tests, a simultaneous injection of glucose and of the octapeptide (1) was made, and the lowering of glycemia with respect to that of control animals which had not received glucose, was followed as a function of time.

The injections were respectively of 0.25 g of glucose and 2 mg per kilo of body weight of the animal, namely about 40 μg, of octapeptide (I) or 20 mg per mouse.

Following the injections, a drop in glycemia distinctly more accentuated was observed in the animals which had received the octapeptide (I).

In the second series of tests, the mice received the product before the injection of glucose. Three injections each of 40μg of octapeptide (1) were administered respectively 72, 48 and 24 hous before the injection of glucose.

As previously, a more rapid drop in glycemia in mice treated with the octapeptide (I) was observed than in control mice receiving only glucose. The effect of this product is hence not only immediate.

e. Effect of the octapeptide (I) on glycemia in diabetic animals

In this test, the drop in glycemia was compared after the simultaneous injection of glucose, on the one hand, and, on the other hand, either of the octapeptide at the dosage of 2 μg (I), or of insulin, or again of both at once. In that latter case the dosage of octapeptide used was also 2μg/g.

The tests were carried out on diabetic rats, kept fasting for 4 hours before the injection of glucose (at the dose of 0.5 g/kg of animal).

The results show that, in animals receiving the octapeptide (I), glycemia is practically unmodified. Glycemia of rats which have received insulin decreases rapidly, stabilises, then rises again after about 120 minutes. For rats receiving both insulin and octapeptide (I), the glycemia decreases distinctly more than with insulin alone and, in addition, the minimum ratio reached is maintained much longer, even beyond 360 minutes after the injection.

f. Mode of Action of the Octapeptide (I)

In an attempt to elucidate the mechanism of action of the octapeptide (I) with respect to insulin, the phenomena were first studied at the level of the insulin receptors of lipid cells trypsinated to destroy said receptors. The trypsinated cells no longer fix the insulin but, if the octapeptide (I) is introduced into the medium, the binking reasppears.

In the same way, the ratio of insulin binding to hepatic cells placed in a suitable reaction medium was measured. When the medium contains octapeptide (I), the ratio of insulin binding to the hepatic cells increases. The result is similar if the said cells are incubated with octapeptide (I).

Finally, the effect of the octapeptide (I) on the glucose receptors of the Langerhans islets was determined. For this purpose, the octapeptide (I) was injected into animals.

One day or four days later, the animals were killed and the islets of Langerhans removed. The latter were placed in a reaction medium supplemented with glucose, and the amount of insulin liberated was determined and compared to controls.

A very substantial increase in the level of the liberated insulin was observed in the Langerhans islet of treated animals.

From all these tests, it seems possible to suggest the following as regards the mode of action of the octapeptide (I):

- it is not active when administered alone, but it potentiates the effects of insulin, even when the latter is in very small amount;
- it induces the synthesis of the receptor sites of insulin, which, it seems, corresponds to the immediate effect (acute effect);
- it sensitises the β cells to glucose; the chronic or permanent effect corresponds to this sensitisation.

g. Tolerance

An acute and subacute toxicity study was carried out on mice for 1 month, each mouse receiving daily dosages corresponding to 5 to 10 times the active dosage. Macro and microscopic studies have not shown any toxic effect under these conditions.

The pharmacological tests described here above show that the compound (I) according to the invention is capable of exerting a regulating action with regard to agents such as somantine, in as much as they would inhibit the regulating effects of insulin with regard to glycemia. They also demonstrate the fact that the compound according to the invention is also capable of potentiating the regulating effect of insulin.

Its pharmacological properties make the compound according to the invention an active therapeutical agent usable either alone or in association with insulin, for the treatment of diabetes. Thus compound (I) can be used for the treatment of diabetes in patients in which the secretion of insulin is normal. In association with insulin, it can also be used for the treatment of diabetes caused in patients in which the action of the secreted insulin is inhibited and those in which it is necessary to obtain a normal glycemia stable in time.

This compound allows the decrease of the dosage of insulin, presently in treatments of diabets for which a high dosage of insulin is necessary.

Finally, it makes it possible to increase the periods of time between the injections.

It may be administered either by injection (intravenous or intramuscular) particularly in the form of a solution for example in a sterile injectable solution, or by the oral route, especially in association with pharmaceutically acceptable solid excipients.

Advantageously, the compound (I) is administered in dosages so as to have a sufficient therapeutic activity, and more particularly in the order of 0.2 to 10 mg/day, advantageously in the order of 1 mg/day.

I claim:

1. The process for the preparation of the octapeptide leucyl—seryl—arginyl—leucyl—phenylalanyl—aspartyl—asparaginyl—alanine of the L-series free of racemized products, by stereospecific condensation, which comprises condensing: (1) (a) the pentapeptide leu—ser—arg—lue—phe— of the L-series with (b) the tripeptide asp—asn—ala of the L-series or (2) (a) the tripeptide leu—ser—arg of the L-series with (b) the pentapeptide leu—phe—asp—asn—ala of the L-series, these amino acids having the respective free amino, hydroxyl, N-guanidino and acid groups blocked to cause them to be inert during the condensation reaction, the condensation being carried out in a solvent for the defined peptides, completing the respective condensations, freeing without degradation the peptide formed of the groups which were blocked during the condensations and isolating the above-defined L-octapeptide.

2. The process of claim 1 which comprises preparing the pentapeptide leu—ser—ag—leu—phe— of the L-series by stereospecific condensation which comprises condensing: (3) (a) the dipeptide leu—phe— with (b) the tripeptide leu—ser—arg— or (4) (a) the dipeptide leu—phe with (b) the tripeptide asp—asn—ala—, these peptides having their respective free amino, hydroxyl, N-guanidino and acid, including terminal acid, groups blocked to cause them to be inert during the condensation reaction, and completing the condensation to form the pentapeptide.

3. The process of claim 2 which comprises freeing without degradation the terminal acid group to make it amenable for condensation.

4. The process of claim 3 wherein the terminal group is freed by acid hydrolysis.

5. The enzymatic method of analytical verification of the stereospecificity of the octapeptide leucyl—seryl—arginyl—leucyl—phenylalanyl—aspartyl—asparaginyl—alanine of the L-series which comprises incubating with (1) chemotrypsin, the octapeptide made in accordance with condensation (1) defined in claim 1 or with (2) trypsin, the octapeptide made in accordance with condensation (2) defined in claim 1, hydrolyzing the octapeptide and collecting the L-amino acids components of the octapeptide free of isomers.

6. The method of claim 1 which comprises incubating a sample of the octapeptide product with (1) chemotrypsin the octapeptide made in accordance with condensation (1) defined in claim 1 or with (2) trypsin the octapeptide made in accordance with condensation (2) defined in claim 1, hydrolyzing the octapeptide and collecting the L-amino acids components of the octapeptide free of isomers.

7. The process of claim 1 wherein condensation is carried out in the presence of hydroxy-benzotriazole, to minimize racemization.

8. The process of claim 1 wherein the condensation is a direct condensation of the carboxylic groups of the peptides condensed.

9. The process of claim 1 wherein the peptides which undergo condensation have an activated hydroxyl group.

10. The process of claim 8 wherein the activated hydroxyl group is esterified.

11. The process of claim 1 of purification of the octapeptide product which comprises subjecting an aqueous solution of the octapeptide to ion-exchange differential chromatography, eluting impurities with water and recovering the highly purified octapeptide with an acid solution.

12. Process of preparation according to claim 1, characterised in that at least one of the amino-acid and/or peptide element condensations is carried out by one of the so-called "activation" methods of carboxylic groups, in manner known in itself.

13. The process for the preparation of the octapeptide leucyl—seryl—arginyl—leucyl—phenylalanyl—aspartyl—asparaginyl—alanine of the L-series free of racemized products, by stereo-specific condensation, which comprises condensing: (1) (a) the pentapeptide leu—ser—arg—leu—phe— of the L-series with (b) the tripeptide asp—asn—ala of the L-series or (2) (a) the tripeptide leu—ser—arg of the L-series with (b) the pentapeptide leu—phe—asp—asn—ala of the L-series, these amino acides having the respective free amino, hydroxyl, N-guanidino and acid groups blocked to cause them to be inert during the condensation reaction, the condensation being carried out in a solvent for the defined peptides, completing the respective condensations, freeing without degradation the peptide formed of the groups which were blocked during the condensations, isolating the above-identified L-octapeptide and carrying out an analytical verification of the stereospecificity of the stereospecificity of the obtained octapeptide leucyl—seryl—arginyl—leucyl—phenylalanyl—aspartyl—asparaginyl—alanine of the L-series, which comprises incubating with (1) chemotrypsin, the octapeptide made in accordance with condensation (1) defined above or with (2) trypsin, the octapeptide made in accordance with condensation (2) defined above, hydrolyzing the octapeptide and collecting the L-amino acids components of the octapeptide free of isomers.

14. The process of claim 1 which comprises condensing first the dipeptide leucyl-phenylalanyl with the tripeptide leucyl—seryl—arginyl, these amino acids having their respective free amino, hydroxyl, N-guanidino and acid groups blocked to be inert during the condensation reaction, freeing one of the end functions of the pentapeptide to permit its condensation to proceed with the tripeptide, as defined in claim 1 formula (1).

15. The process of claim 15 which comprises the condensation of the peptide fragments as defined in claim 1 formula (2).

16. The process of claim 1 wherein the condensation is carried out in the presence of dicyclohexylcarbodiimide.

17. The process of claim 15 wherein the condensation is carried out in the presence of dicyclohexylcarbodiimide.

18. The process of claim 16 wherein the condensation is carried out in the presence of dicyclohexylcarbodiimide and of hydroxbenzotriazole.

19. The process of purification of the L-octapeptide product of claim 11 which comprises placing the L-octapeptide product in an aqueous solution, passing it over a chromatographic column filled with carboxymethylcellulose, eluting the impurities with water and an approximately 0.05 M acetic acid solution, and eluting the octapeptide with a 1 M acetic acid solution.

20. The process of claim 2 which comprises the condensation of the peptide fragments defined in claim 13 (3) (a) and (b).

21. The process of claim 2 which comprises the condensation of the peptide fragments defined in claim 13 (4) (a) and (b).

* * * * *